US007540656B1

(12) United States Patent
Stochl et al.

(10) Patent No.: US 7,540,656 B1
(45) Date of Patent: Jun. 2, 2009

(54) APPARATUS FOR DIRECT MEASUREMENT OF INSULATION THERMAL PERFORMANCE AT CRYOGENIC TEMPERATURES

(75) Inventors: Robert J. Stochl, Middleburg Heights, OH (US); Matthew E. Moran, Friendswood, TX (US); Alexander J. Yeckley, Castalia, OH (US)

(73) Assignee: Sierra Lobo, Inc., Fremont, OH (US)

( * ) Notice: Subject to any disclaimer, the term of this patent is extended or adjusted under 35 U.S.C. 154(b) by 105 days.

(21) Appl. No.: 11/627,783

(22) Filed: Jan. 26, 2007

Related U.S. Application Data

(60) Provisional application No. 60/762,274, filed on Jan. 26, 2006.

(51) Int. Cl.
  *G01N 25/00* (2006.01)
  *G01K 17/00* (2006.01)
(52) U.S. Cl. .................................. 374/29; 374/5; 374/31
(58) Field of Classification Search .................... 374/29, 374/5, 31
  See application file for complete search history.

(56) References Cited

U.S. PATENT DOCUMENTS 3,733,887 A * 5/1973 Stanley et al. .................. 374/44

5,940,784 A * 8/1999 El-Husayni .................. 702/130
6,487,866 B1 * 12/2002 Fesmire et al. ............... 62/51.1

OTHER PUBLICATIONS

ASTM International, Designation: C 177-04, "Standard Test Method for Steady-State Heat Flux Measurements and Thermal Transmission Properties by Means of the Guarded-Hot-Plate Apparatus". 2004, 21 pages.
International Standard, ISO 8302, "Thermal Insulation—Determination of Steady-State Thermal Resistance and Related Properties—Guarded Hot Plate Apparatus," 1991, 54 pages.

* cited by examiner

*Primary Examiner*—Gail Verbitsky
*Assistant Examiner*—Mirellys Jagan
(74) *Attorney, Agent, or Firm*—Pearne & Gordon LLP

(57) ABSTRACT

An apparatus for measuring insulation thermal performance is provided, particularly between ambient and cryogenic temperatures. A warm-temperature boundary has a continuous sample contact surface that is divided into a metered central zone and a boundary guard zone. Each zone is independently heated, and the power necessary to maintain the central zone at constant temperature is directly equated to heat flux through the insulation at the temperature boundary conditions. Methods for measuring insulation thermal performance are also disclosed.

29 Claims, 6 Drawing Sheets

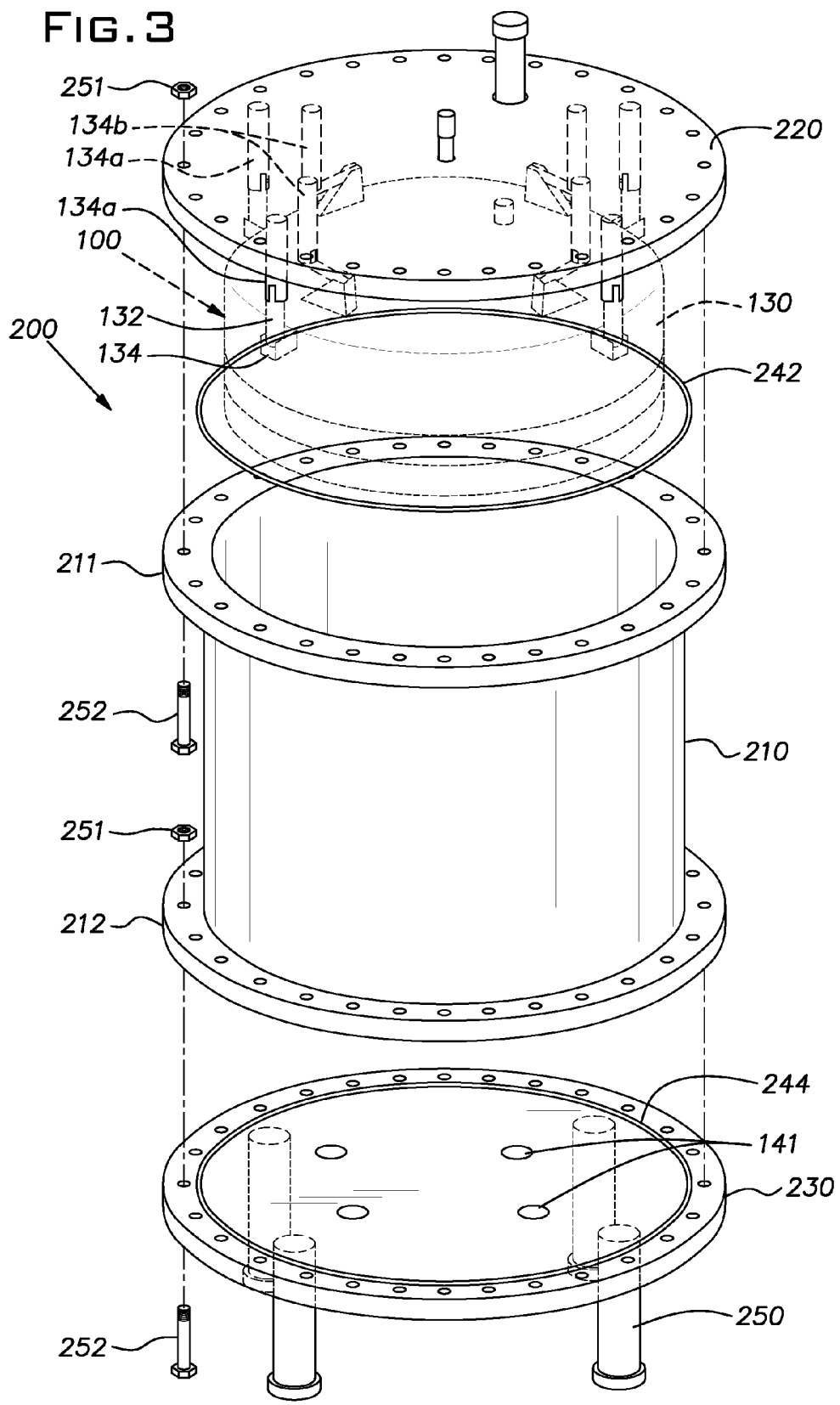

US 7,540,656 B1

APPARATUS FOR DIRECT MEASUREMENT OF INSULATION THERMAL PERFORMANCE AT CRYOGENIC TEMPERATURES

CROSS-REFERENCE TO RELATED APPLICATIONS

This application claims the benefit of U.S. Provisional Patent Application Ser. No. 60/762,274 filed Jan. 26, 2006, the contents of which are incorporated herein by reference.

STATEMENT OF GOVERNMENT SPONSORED RESEARCH

This invention was made with government support under contract No. F29601-02-C-0186 awarded by the U.S. Air Force Research Laboratory, Kirtland Air Force Base, Albuquerque, N. Mex. The government has certain rights in this invention.

BACKGROUND OF THE INVENTION

1. Field of the Invention

The present invention relates to an apparatus for directly measuring insulation thermal performance at cryogenic temperatures. More particularly, it relates to such an apparatus that facilitates accurate performance determinations without measuring or quantifying cryogenic material boil-off.

2. Description of Related Art

The ability to store large amounts of cryogenic fluids for long durations will have a profound effect on the success of many future space programs using propellant, reactant, and life support cryogens. These missions will require on-orbit systems capable of long-term storage of cryogens for applications such as: space platforms using electric propulsion, space-based lasers, orbit-transfer vehicles, and orbital-propellant depots. The high cost of delivering payload mass to orbit will require storage systems capable of significantly limiting cryogenic losses due to boil-off, particularly for mission durations of up to ten years or longer.

High performance insulation systems are essential to meet these low boil-off requirements. For missions that require zero or near-zero boil-off, the performance of passive insulation systems must be maximized in order to minimize the power requirement of an active refrigeration system. Although Multi-Layer Insulation (MLI) systems have been extensively used to insulate cryogenic vessels in a space environment, it has been for short-duration missions that require from 30 to 50 layers to meet the mission requirements. Conversely, 150 layers or more of MLI will likely be needed to meet the requirements of future long-term missions. Limited data exists on the performance and physical characteristics of these thick MLI systems.

Optimization of the passive insulation systems using thick MLI will be required to minimize the mass, volume, and power consumption of any active cooling technologies. Current passive insulation systems are unable to meet the thermal performance needs of future space missions requiring long-term storage of cryogenic fluids. Critical information on the performance of thick MLI systems—a fundamental requirement—is lacking. Therefore, systematic investigation of thick MLI performance at liquid hydrogen temperatures would provide an opportunity to quantify vitally needed data for future missions. The ability to test with liquid hydrogen (LH$_2$) is desirable, because LH$_2$ represents the coldest cryogenic liquid planned for most missions and would, therefore, verify thick MLI performance for the most challenging applications.

Disclosed herein is an apparatus that measures insulation thermal performance, including thick MLI systems, that does not rely on measurement of cryogenic liquid boil-off to calculate insulation thermal performance, thereby avoiding the inherent difficulties to a) eliminate ambient heat leak into a cryogenic tank that bypasses the insulation (which will introduce errors in the heat flux calculations), and b) precisely measure very low boil-off flow rates.

SUMMARY OF INVENTION

An apparatus to measure insulation thermal performance includes a warm-temperature boundary having a continuous sample contact surface and a cold-temperature boundary. The continuous sample contact surface has a central metered zone and a boundary guard zone surrounding the central metered zone. Both the central metered zone and the boundary guard zone are heated zones. The central metered zone is heated independently of the boundary guard zone. The apparatus is adapted to accommodate a sample of insulation between the sample contact surface and the cold-temperature boundary for measuring heat flux through the sample.

A method for measuring thermal performance of a sample of insulation is also provided. The method includes the steps of: providing a heater arrangement having a continuous sample contact surface that has a central metered zone and a boundary guard zone surrounding the central metered zone, wherein both of the zones are heated zones and the central metered zone is heated independently of the boundary guard zone; providing a cryogenic storage vessel having an outer surface; disposing a sample of insulation between the sample contact surface and the storage vessel outer surface; separately maintaining the central metered zone and the boundary guard zone at a constant warm-boundary temperature; measuring the power required to separately maintain the central metered zone at the constant warm-boundary temperature; and equating that power to heat flux through the sample of insulation.

BRIEF DESCRIPTION OF THE DRAWINGS

FIG. 3 is an exploded perspective view of a vacuum chamber assembly of the apparatus of FIG. 1.

FIG. 7 shows a schematic plan view of heating elements 128a and 128b, according to an embodiment where element 128b is provided as an array of segmented flexible printed circuits surrounding the element 128a.

DETAILED DESCRIPTION OF THE PREFERRED EMBODIMENTS OF THE INVENTION

As used herein, when a range such as 5 to 25 (or 5-25) is given, this means preferably at least 5 and, separately independently, preferably not more than 25. Unless otherwise specified, all components described herein are made from conventional materials in a conventional manner.

An apparatus is provided to measure the heat flux through a sample of insulation at selected boundary conditions, wherein one of the boundaries is maintained at a cryogenic temperature. The apparatus facilitates accurate measurement of thermal performance of the insulation under the desired test conditions. The data collected for a particular insulation arrangement using the disclosed apparatus can be used to approximate or estimate the performance of the same insulation under real-world conditions, such as to insulate a cryogenic fluid tank for in-orbit or deep-space missions. Alternatively, data can be used to estimate insulation performance for earth-based applications.

Figure 1:
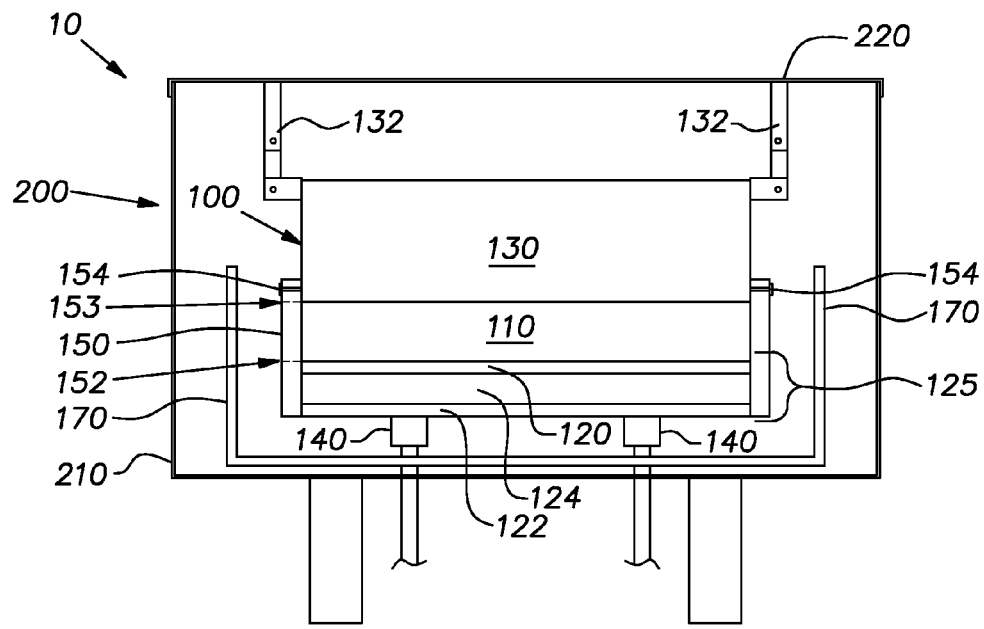
FIG. 1 is a side schematic view of an apparatus for direct measurement of insulation thermal performance.

Referring first to FIG. 1, an apparatus 10 for direct measurement of insulation thermal performance is shown schematically. In the illustrated embodiment, an insulation measurement assembly 100 is located within a vacuum chamber 200. The insulation measurement assembly 100 includes a warm-temperature boundary in spaced arrangement with a cold-temperature boundary. In the illustrated embodiment, the warm-temperature boundary is provided by a heater arrangement 125, and the cold-temperature boundary is provided by a cryogenic storage vessel or tank 130. In use, the sample of insulation 110 whose performance is to be measured is disposed in between the warm- and cold-temperature boundaries. As explained below, heat flux through the insulation is measured based on the power required to maintain the warm-temperature boundary (or a portion thereof) constant at the boundary temperature. No measurement of boil-off rates of cryogenic material from the storage vessel 130 is required as part of the heat-flux measurement.

The insulation measurement assembly is disposed within a vacuum chamber 200. The vacuum chamber 200 permits simulation of the vacuum of orbital and deep-space applications. Operating the measurement assembly 100 in a vacuum also simulates the conditions used for many earth-based cryogenic insulation applications; whereby the insulation is contained within a vacuum jacket to minimize heat transfer by convection and molecular gas conduction. This way, the performance of the insulation sample 110 to inhibit heat transfer between the two boundary conditions (provided by heater arrangement 125 and tank 130, described below) can be measured as accurately as possible. The vacuum chamber 200 will be described more fully below.

Figure 2:
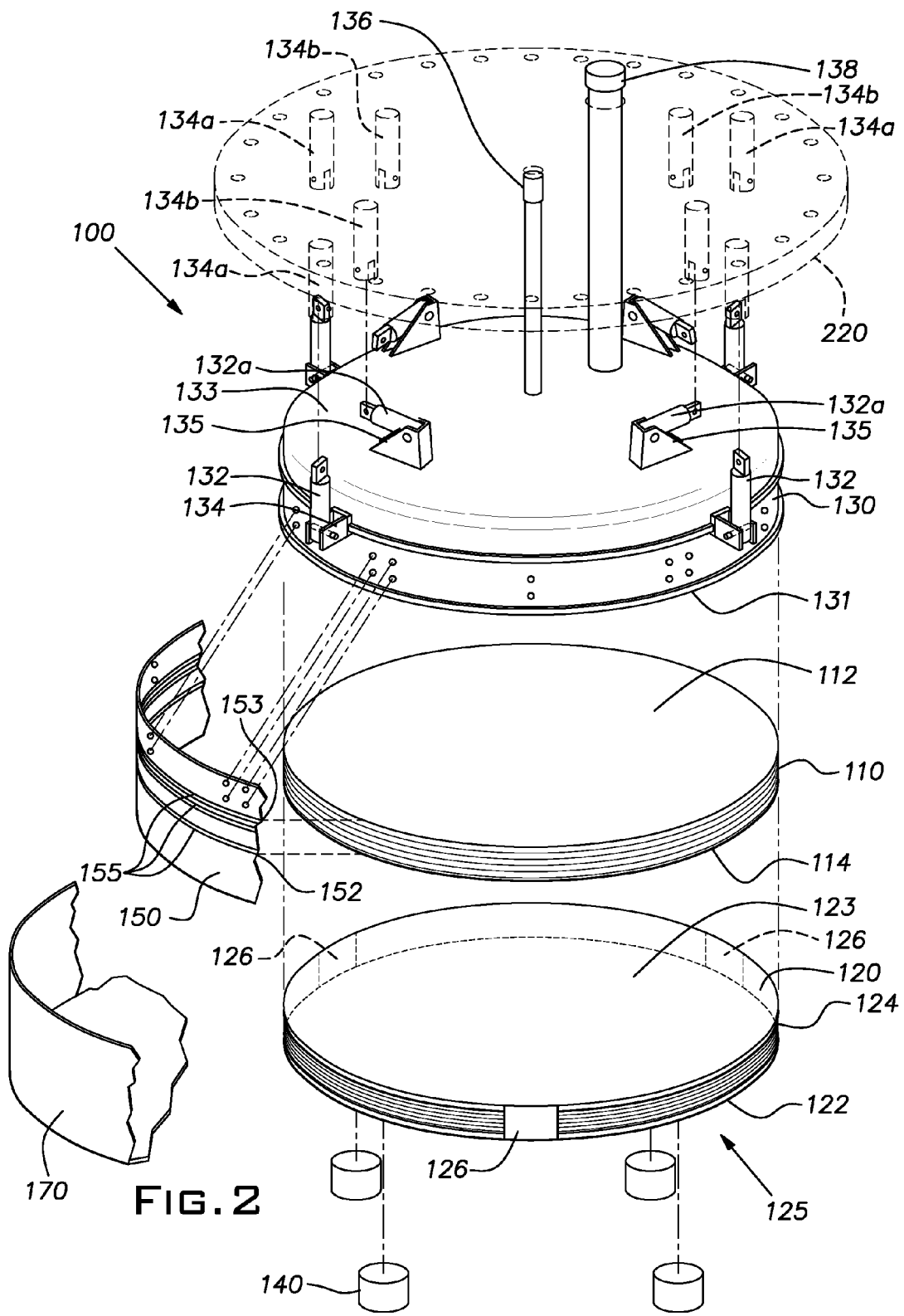
FIG. 2 is an exploded perspective view of an insulation measurement assembly of the apparatus of FIG. 1.

Returning to the insulation measurement assembly 100, FIG. 2 illustrates a perspective exploded view of an embodiment thereof. The assembly 100 includes two primary components as mentioned above: the cryogenic storage vessel 130 and the heater arrangement 125. The insulation sample 110 whose performance is to be measured is disposed in between these two components as illustrated and also mentioned above. During operation, the insulation sample 110 is sandwiched between the vessel 130 and arrangement 125 to provide as uniform as possible surface-to-surface contact between the former and the upper surface of the insulation sample 110, and between the latter and the lower surface of the insulation sample 110. Both the vessel 130 and the heater arrangement 125 will now be described in detail.

The cryogenic storage vessel 130 can be provided in accordance with conventional vessels for storing a cryogenic fluid, such as liquid helium, liquid hydrogen, liquid oxygen, liquid nitrogen, etc. The specific material of construction and wall thickness for the vessel 130 can be selected based on known or conventional criteria depending on the particular liquid cryogen or cryogens that will be stored in the vessel 130. The purpose of the liquid cryogen is to provide the desired cold-boundary temperature at the outer bottom wall surface 131 of the vessel 130. Common cryogenic liquids that can be used include helium, hydrogen, oxygen and nitrogen. Alternatively, other cryogenic materials can be used where it is desirable to simulate a precise cold-boundary temperature different from that which would be achieved from any of the four cryogens mentioned above. The criteria for constructing the vessel 130, including material of construction, should be selected based on the cryogen or cryogens that will be used to provide the desired cold-boundary temperature. Such criteria can be found in the literature for various cryogenic materials.

The vessel 130 preferably has a planar bottom wall with a flat, planar outer bottom wall surface 131. This outer wall surface 131 is the surface that will be in contact with the upper surface 112 of the insulation sample 110 during operation of the apparatus. It is also preferred that the bottom wall (and its outer wall surface 131) of the vessel 130 be circular. Accordingly, in this embodiment the vessel 130 preferably is a substantially cylindrical vessel with a flat, circular bottom wall. The upper wall 133 of the vessel 130 can be dome-shaped as shown in FIG. 2. A fill pipe 136 is provided for filling the vessel 130 with a cryogenic liquid. A vent 138 is also provided, to relieve cryogenic gas overpressure and accommodate boil-off of the cryogenic liquid. Significantly, as will be further described below, no apparatus or device need be provided to measure the amount of cryogenic material that is vented as a result of boil-off.

A series of brackets 134 are fixed to the vessel 130 to accommodate suspension brace members 132. The brackets 134 are provided and positioned so that the entire weight of the vessel 130 and the cryogenic liquid within it can be supported from above via the brace members 132. In the illustrated embodiment, the brackets 134 are fixed about the circumference of the vessel 130, and spaced equal radial distances from one another. Four such brackets 134 are shown in FIG. 2, which are spaced $\pi/2$ radians (90°) apart. Whatever the arrangement of brackets 134, it should be such as to ensure uniform distribution of the weight of the vessel 130 and its contents among them when suspended from above. Thus, brackets 134 and brace members 132 support the weight of the vessel 130. In addition, it is further desirable to include brackets 135 and associated lateral brace members 132a (connected to associated brackets 134b suspended from the lid 220) to counteract lateral and torsional loads that may otherwise act to shift the vessel 130 laterally, which may cause the vessel 130 to go out of registry with the heater arrangement 125 (described below). Preferably, the brace members 132 and 132a are made from a low-thermal-conductivity material, so as to minimize heat leak into the cryogenic storage vessel 130, which can result in wasteful boil-off of the cryogenic material within. In the illustrated embodiment, lateral-support brackets 135 are secured to the upper domed surface of the storage vessel 130, and angled so that the lateral brace members 132a will be effective to counteract torsional loads. The lateral brace members 132a are secured at their opposite ends to respective brackets 134b that extend downward in alignment with the lateral brace members 132*a*, to be secured thereto in order to brace against lateral or torsional loads.

Figure 4A:
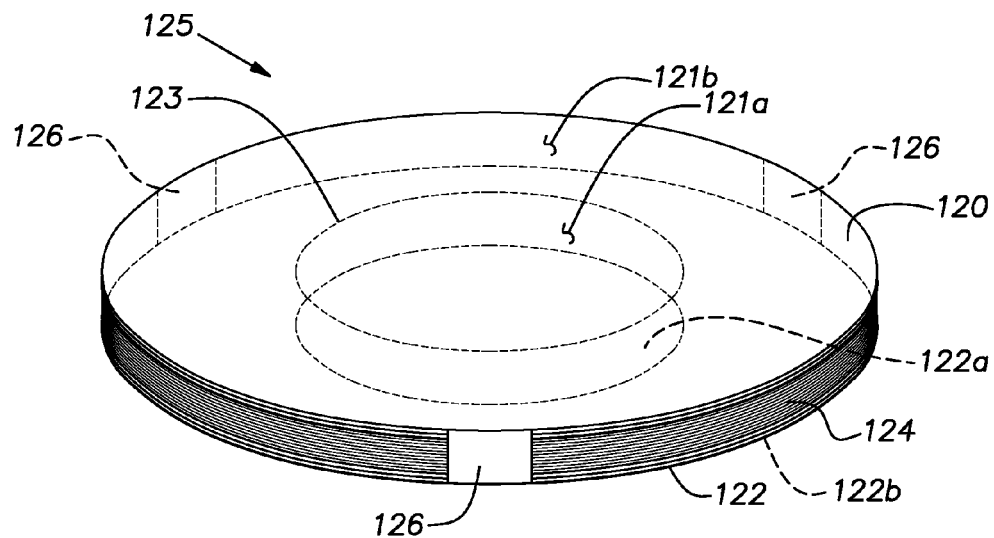
FIGS. 4a-b show an isothermal heater arrangement in perspective and edge views, respectively.
Figure 4B:
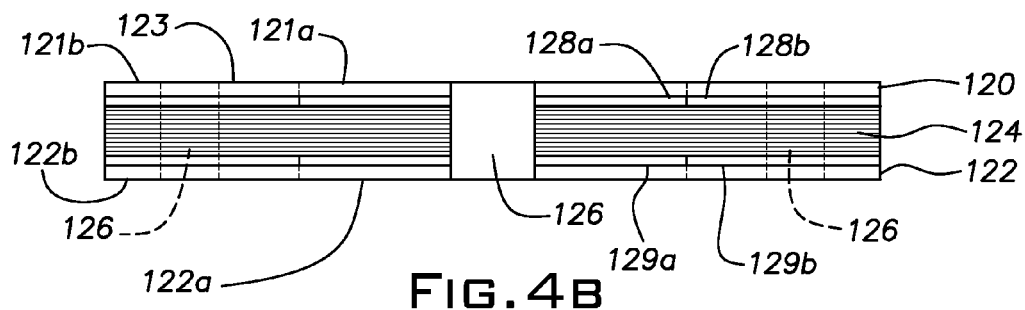

The heater arrangement 125, also seen in FIG. 2, and more clearly illustrated in FIGS. 4*a*-4*b*, includes a first or upper heater plate 120 and a second or lower heater plate 122. The upper and lower heater plates 120 and 122 are preferably the same shape, preferably circular and having the same diameter as the outer bottom wall surface 131. In one embodiment, the diameter of the plates 120 and 122 is 40-60 inches, more preferably 45-55 inches, and most preferably 50 inches to minimize edge effects. The upper and lower heater plates 120 and 122 are coextensive and in register with one another, fixed in spaced parallel relationship, for example via brackets 126. Both the upper and lower heater plates 120 and 122 are made of a thermally conductive material, such as metal, for example aluminum, copper or steel. The heater plates 120 and 122 preferably have the same thickness, preferably 0.25 to 1.0 inches, preferably 0.25 to 0.50 inches, more preferably about 0.25 inches. Alternatively, their thicknesses need not be the same.

The upper heater plate 120 is a continuous plate of thermally-conductive material, having a continuous sample contact surface 123 as its upper surface. The continuous sample contact surface 123 (and heater plate 120) is divided into two heating zones as shown by the broken line in FIG. 4*a*, namely a central metered zone 121*a* and a boundary guard zone 121*b*. In a preferred embodiment, the central metered zone 121*a* is a circular zone at the center of the surface 123, and the boundary guard zone 121*b* is an annular zone surrounding the central zone 121*a*. A first planar heating element 128*a* (illustrated in FIG. 4*b*) is provided in contact with the upper heater plate 120, and is coextensive and in register with the central metered zone 121*a* of the contact surface 123. A second planar heating element 128*b* is provided in contact with the upper heater plate 120, and is coextensive and in register with the boundary guard zone 121*b* of the contact surface 123. Preferably, the planar heating elements 128*a* and 128*b* are contacted with the surface of the upper heater plate opposite the contact surface 123, so that the sample of insulation 110 can rest directly on and in contact with the contact surface 123. The lower heater plate 122 also is a continuous plate of thermally conductive material. It is not critical that the lower heater plate 122 be divided into separately-heated zones similar to the upper heater plate 120, although it is preferred. That is, the lower heater plate 122 preferably also includes a central zone 122*a* and a boundary guard zone 122*b*, wherein zones 122*a* and 122*b* of the lower heater plate 122 are respectively coextensive and in register with the zones 121*a* and 121*b* of the upper heater plate 120. In this embodiment, third and fourth planar heating elements 129*a* and 129*b* are provided in contact with the lower heater plate 122, respectively coextensive and in register with the central and boundary guard zones 129*a* and 129*b*. Alternatively, if the lower heater plate is not to include separately-heated zones, than only a one planar heating element may be used and provided in contact and in register with the full expanse of the lower heater plate 122. Separately-heated zones 129*a* and 129*b* are preferred because this permits more precise metering of the temperature across the entire surface of the lower heater plate 122 to achieve a common setpoint temperature that does not vary radially, or that varies as minimally as possible.

Figure 7:
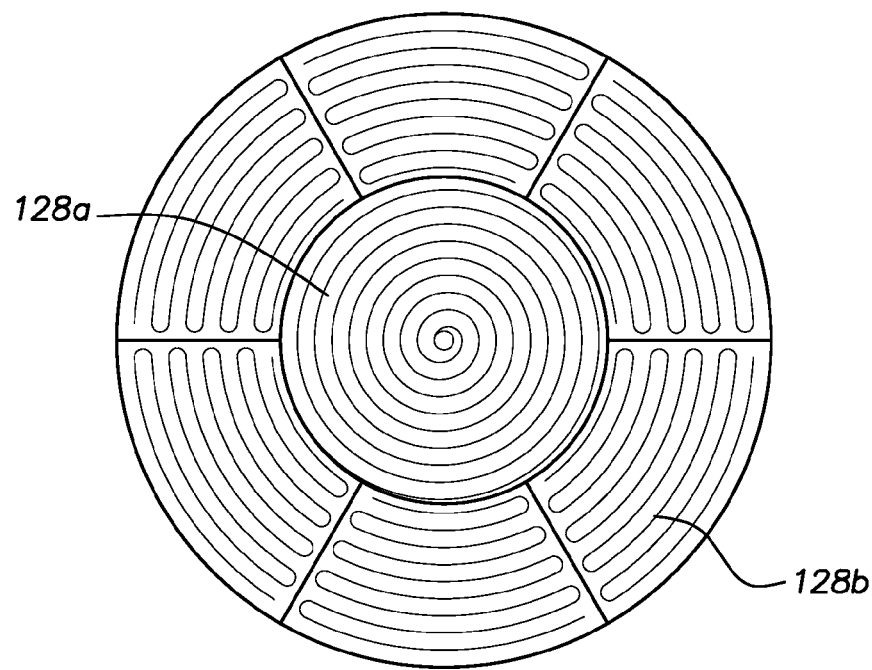

The heating elements described above can be composed of flexible printed circuits having resistive copper traces. The geometry of those traces (including width, thickness and path) is selected in order to provide a uniform heat flux into the plates 120 and 122 upon application of a controlled electrical current. The trace geometry of heating element 128*a* preferably includes a spiral-wound copper trace wherein adjacent windings are preferably concentric and evenly spaced from one another a shown in FIG. 7. Alternatively, instead of a true spiral, the trace for the heating element 128*a* can be alternately serpentine-wound with each successive winding completing nearly a complete circle before reversing course to complete the next-successive winding. This will produce a near-serpentine geometry similar though not identical to that illustrated in FIG. 7. Heating element 128*b* can be formed from an array of planar, flexible printed circuit segments aligned around the heating element 128*a*, as shown in FIG. 7. Each segment forming the heating element 128*b* includes a resistive serpentine copper trace having concentric and evenly spaced arcs as shown in FIG. 7. The serpentine traces in each segment forming the heating element 128*b* are electrically connected in series such that a single resistive circuit is formed for heating element 128*b*. Each flexible printed circuit heating element 128*a* and 128*b* is laminated or adhered in continuous, uniform contact with the upper heater plate 120, preferably using a 1 mil thick adhesive layer suitable for use in vacuum and cryogenic environments. Alternatively, a single, continuous printed circuit heating element can be used for the heating element 128*b*. The segmented embodiment described in this paragraph and illustrated in FIG. 7 is preferred when the dimensions of the heater plate 120 are large enough that manufacturing a single, continuous heating element 128*b* of the appropriate size would be difficult or undesirable. It will be appreciated that heating elements 129*a* and 129*b* can be provided and adhered to the lower heater plate 122 substantially similarly as described in this paragraph.

As more fully described below, the performance of a sample of insulation 110 is determined by measuring the power input to the first (central zone) heating element 128*a* necessary to maintain the central metered zone 121*a* of the heater plate 120 (specifically contact surface 123) constant at the warm boundary temperature. Accordingly, it is desirable to minimize or eliminate heat flux to and from the central metered zone 121*a* except between that zone and the sample of insulation 110 directly above. Accordingly, both the boundary guard zone 121*b* of the upper heater plate, and the lower heater plate 122, are maintained at the same temperature as the central metered zone 121*a*, to eliminate temperature gradients in both radial and downward directions. The result is constant-temperature, adiabatic operation of the central metered zone 121*a*, except for heat flux through the sample of insulation 110, toward the cold-temperature boundary at the outer bottom wall surface 131 of the cryogenic storage vessel 130.

The second (annular) heating element 128*b* is operated to maintain the boundary guard zone 121*b* at the same temperature as the central metered zone 121*a* during operation, i.e. the warm boundary temperature. It will be recognized that the metered zone 121*a* and the boundary guard zone 121*b*, though separately heated, are different portions of the same continuous sample contact surface 123 and heater plate 120. Making these zones continuous eliminates boundary heat-transfer effects between the two zones that would be present if they were separated or discontinuous zones that were insulated from one another. Making the zones continuous also eliminates the uncertainty in measuring the edge heat-transfer effects between the central zone and the boundary guard zone. Such errors would introduce unpredictable errors into the calculation of heat flux for the insulation sample 110. Preferably, the dimensions of the central metered zone 121*a* and the boundary guard zone 121*b* are selected so as to minimize edge heat-transfer effects between those zones. This is most easily achieved by selecting the dimensions so that the temperature on either side of the zone boundary is constant, under the prevailing conditions of the test. Ideally, the central metered zone 121a is sufficiently large to provide an appreciable surface area for calculation of flux, but sufficiently recessed from the outer edge of the heater plate 120 so that edge heat-transfer effects from the outer edge are not seen at the metered zone-guard zone interface; i.e. so that the temperature gradient across the boundary between zones 121a and 121b is zero or substantially zero. In the preferred embodiment wherein the heater plate 120 (and sample contact surface 123) is circular and has a diameter of 50 inches, a central metered zone 121a diameter of 30 inches may be desirable.

Flux is heat transfer rate per unit area. By separately metering the central and guard zones 121a and 121b, it is possible to calculate heat flux through the insulation sample 110 based solely on the area of the central metered zone 121a and the power supplied to maintain that zone 121a at the constant warm-boundary temperature. Because flux is measured based on power supplied to the central zone 121a only, edge heat transfer effects are substantially eliminated because there is no temperature gradient at the boundary of the central zone 121a. That is, because the central zone 121a and guard zone 121b are continuous, with no discrete boundary, there is no boundary temperature gradient and negligible or substantially zero heat transfer to or from the central zone 121a in a radial (or planar) direction. Accordingly, there are negligible or substantially zero radial heat transfer effects that need to be accounted for when equating the power supplied to first heating element 128a (to maintain the temperature of the central zone 121a) to the heat flux through the sample of insulation 110. Edge heat transfer effects at the edge of the boundary guard zone 121b are not seen at the edge of the central zone 121a, or at least their impact is minimized by separately operating the second heating element 128b to maintain the guard zone 121b at the same temperature as the central zone 121a.

As mentioned above, the heating element(s) on the lower heater plate 122 is/are operated to maintain the temperature of the lower heater plate 122 constant at the warm-boundary temperature (the same temperature as the central zone 121a of the upper heater plate 120). The result is a zero temperature gradient between the two heater plates 120 and 122, meaning that heat flux from the upper plate 120 (central zone 121a) downward is also substantially zero. The space between the upper and lower heater plates 120 and 122 is filled with an insulation material 124, to dampen any instantaneous changes or variances between the time-average temperatures of the upper and lower heater plates 120 and 122, which should be the same and constant. In a preferred embodiment, the insulation material (MLI) consists of alternating layers of double-aluminized Mylar™ insulation with Dacron™ netting spacers sufficient to fill the space. ("Mylar" and "Dacron" are registered trademarks). The distance or spacing between the heater plates 120 and 122 should be selected, in conjunction with any insulating material provided therebetween, to provide adiabatic or substantially adiabatic operation of the upper heater plate 120 in the downward (toward lower heater plate 122) direction at the warm-boundary operating temperature. In one embodiment, the upper and lower heater plates 120 and 122 are spaced approximately 2.0 inches apart, wherein it has been found that about 200 layers of MLI insulation with Dacron netting spacers is sufficient.

In summary, it will be recognized that the heater arrangement 125 is configured so that the central metered zone 121a of the upper heater plate 120 is operated adiabatically at the designated warm-boundary temperature, except for heat flux toward the cold-temperature boundary through a sample of insulation 110. Accordingly, the power consumed to maintain the central zone 121a constant at the warm-boundary temperature, which can be accurately measured, provides a very good estimate of the performance of the insulation sample 110 (i.e. its effective thermal conductivity or effective 'k') based on heat flux through that sample under the given MLI boundary temperature conditions.

As explained above, the insulation measurement assembly 100 is located within vacuum chamber 200. Referring to FIG. 3, an embodiment of such a vacuum chamber 200 is illustrated. The chamber 200 includes a cylindrical vacuum housing 210 having upper and lower sealing flanges 211 and 212. The sealing flanges 211,212 can be integrally formed to the cylindrical housing 210 or they can be secured thereto in a manner that will be leak-tight under vacuum, such as through welding. A vacuum base 230 and a vacuum lid 220 are also provided, and are adapted to mate with the corresponding sealing flange 212 and 211, respectively. Preferably, vacuum sealing gaskets 242 and 244 are provided respectively between the lid 220 or base 230 and the associated sealing flange 211 or 212, in order to provide a leak-tight vacuum seal when the vacuum chamber 200 is fully assembled. The vacuum base 230 is secured to the lower sealing flange 212 via conventional means, for example via nut and bolt fasteners 251,252 as known in the art. Alternatively, other suitable securements or fasteners could be used, for example clamps. The vacuum lid 220 is similarly secured to the upper sealing flange 211, via suitable means. The entire vacuum chamber 200 can be supported via conventional chamber support members or legs 250.

Figure 8:
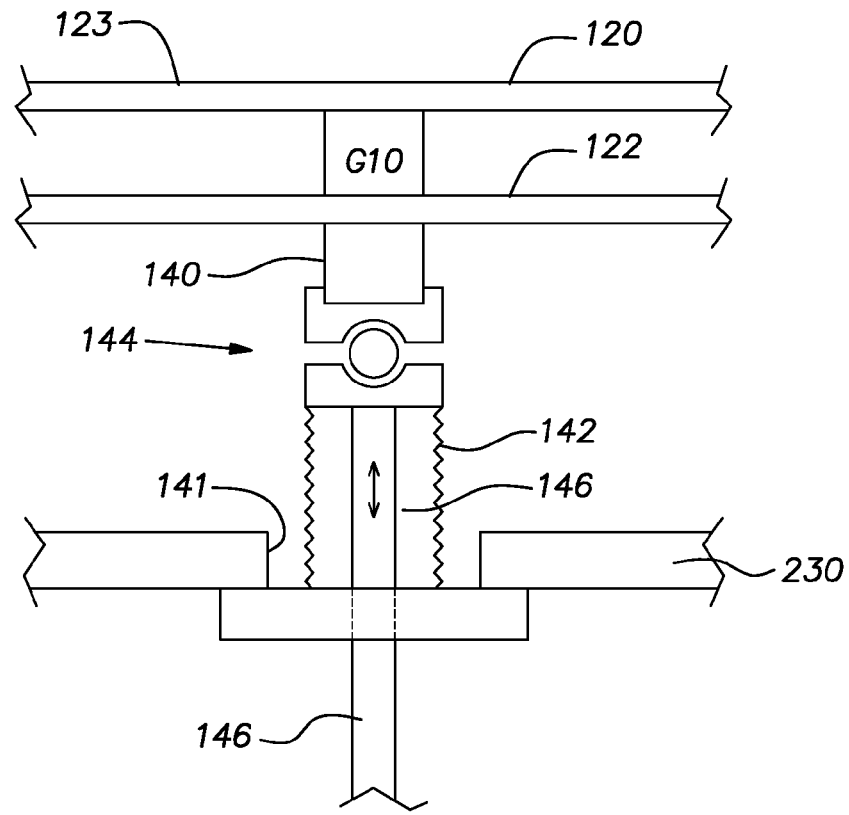
FIG. 8 shows a schematic view of a height adjustment mechanism for adjusting the height and/or planar orientation of the heater arrangement 125, and more particularly the sample contact surface 123.

In a preferred embodiment, the cryogenic storage vessel 130 of the insulation measurement assembly 100 is suspended from the underside of the vacuum lid 220, e.g. via brace members 132. The heater arrangement 125 is supported from underneath via support members 140, which are preferably made of a heat-insulating material, for example G-10. The support members 140 are provided and arranged (positioned) so as to minimize the deformation of the heater arrangement 125 or the plates 120 and 122 thereof due to their own weight. In one embodiment, spacers formed of insulating material, for example G-10, are disposed in between the heater plates 120 and 122 at the locations where the heater arrangement 125 is supported via support members 140, to prevent deformation between the plates 120 and 122. In the preferred embodiment wherein the heater plates 120 and 122 are circular, the support members 140 can be arranged circumferentially equidistant from one another at a constant radius from the center of the heater plate 122. In a preferred embodiment, the vertical position of the heater arrangement 125 within the vacuum chamber 200 can be adjusted at each support member 140, so that the heater arrangement 125 can be raised or lowered relative to the cryogenic storage vessel 130 suspended thereabove, with the sample of insulation 110 disposed in between. The preferred mechanism for height adjustment is illustrated in FIG. 8. Though FIG. 8 illustrates only a single height adjustment mechanism coupled to a single one of support members 140, it will be appreciated that the same mechanism applies equally to all the support members 140 that support the heater arrangement 125.

Each support member 140 is coupled to a vertical actuator device 146 via a gimbal joint 144, as shown schematically in FIG. 8. The vertical actuator device 146 can be a telescoping leg member or other mechanical structure capable to raise and lower the gimball joint 144, and thereby the support member 140 supported thereon. It will be appreciated that in this embodiment, wherein the height of each support member 140 is independently controlled via a separate actuator device 146 via gimbal joints 144, the height and planar orientation of the heater arrangement 125 can be independently controlled based on the independent positioning of each actuator. The exact design of the actuator devices 146 is not critical, and numerous mechanisms will be readily known or devisable by the person of ordinary skill in the art without undue experimentation. For example, vertical adjustment can be achieved by a telescoping inner leg member that is telescopically received within an outer or sleeve leg member, as illustrated schematically in FIGS. 5a-5c (described below). Servo motors, stepper motors or other conventional adjustment mechanisms could be used to adjust the height of each support members 140 (via gimbal joint 144 and through bellows 141) by adjusting the telescopic position of the inner member. Alternatively, other mechanisms could be used, for example a hydraulic lift mechanism.

It may be desirable to locate the actuating/controlling mechanism, e.g. motors, gears, circuitry, etc. (not shown), for raising and lowering the actuator device 146 outside the vacuum chamber 200. For example, the operation of such a mechanism under vacuum conditions may create additional engineering problems that can be avoided. In addition, if the actuator device 146 is to be an extensible leg, then it may be desirable that it can extend beyond the base 230 of the vacuum chamber 200, depending on the degree of desired up/down adjustability of the heater arrangement 125. In either case, the support members 140 can be aligned with openings 141 through the base 230 of the vacuum chamber 200. Each opening 141 can accommodate the associated vertical actuator device 146 therethrough, which also permits one to locate actuating equipment (motors, etc.) outside of the vacuum chamber 200. In this embodiment, to maintain a vacuum seal despite the opening 141, an expansible/contractible bellows 142 is disposed around the actuator device 146, to expand and contract as that device 146 is raised or lowered, respectively. The bellows 142 can be secured at its lower end either to a sealing flange that seals the opening 141 (and through which the device 146 extends) as shown, or alternatively to the base 230 itself around the opening 141 (not shown). It should be further noted that if hydrogen or another combustible fuel source is to be used as the liquid cryogen in vessel 130 to supply the cold-boundary temperature, all electrical or motor components that may provide a spark or other ignition source should be disposed in suitable enclosures and/or blanketed with nitrogen or other inert gas, so they are isolated from any combustible fuel that may be vented from the vessel 130 (or leaked from vacuum chamber 200) into the environment.

The resulting support system allows the heater arrangement 125 (and sample contact surface 123) to be adjustable to any required plane orientation or elevation. The vertical position of each actuator device 146 can be chosen based on feedback from individual contact sensors located between the upper surface 112 of the insulation sample 110 and the outer bottom wall surface 131 of the vessel 130, or other cold-temperature boundary surface. Via a feedback control architecture, this support system can thus detect and compensate for any planar misalignment between those surfaces resulting from non-uniform thermal contraction of the vessel 130, non-uniform relaxation of the insulation sample 110 (e.g. MLI) in a vacuum, manufacturing imperfections, or other causes.

To test a sample of insulation 110, the sample 110 is disposed and rests on the sample contact surface 123. The sample of insulation 110 preferably has the same lateral dimensions as that surface 123 as well as the outer bottom wall surface 131 of the vessel 130, and is arranged so as to be in register therewith. The cryogenic storage vessel 130, which is suspended from above, preferably from the lid 220 of the vacuum chamber 200 (described below), is lowered over the insulation 110 until the upper surface 112 of the insulation 110 comes into contact with the outer bottom wall surface 131. Alternatively, the storage vessel 130 is lowered into a fixed position, and then the sample contact surface 123 is raised (e.g. via adjustable support members 140) so that the upper surface 112 of the insulation 110 contacts the surface 131. If the storage vessel 130 is suspended from the vacuum lid 220 as shown, the vacuum lid 220 is carefully lowered so that the cryogenic storage vessel 230 is also lowered into position, taking care to maintain the co-registry of the storage vessel 230, insulation sample 110 and heater plate 120. Once it has been lowered in place, the lid 220 is secured to the housing 210. If necessary, the support members 140 are actuated to raise the heater arrangement 125 so that the upper surface 112 of the sample of insulation 110 contacts the outer bottom wall surface 131 of the vessel 130. The result is the sample of insulation 110 is disposed in between and provided in contact with the outer bottom wall surface 131 (cold-temperature boundary) at its upper surface 112, and the sample contact surface 123 of the upper heater plate 120 (warm-temperature boundary) at its lower surface 114. The cryogenic vessel 130 is filled with a cryogenic liquid to provide the desired cold-boundary temperature at the outer bottom wall surface 131. The heating elements are activated and operated to bring the upper heater plate 120 (both zones) and the lower heater plate 122 (both zones if applicable) to the desired constant warm-boundary temperature.

Depending on the thermal conductivity of the vessel 130 walls and the heater plates 120 and 122, as well as the effectiveness of the insulation 110 being tested, it may take hours to days, or perhaps even weeks, to achieve steady state. Once steady state has been reached, power consumption to maintain both the central metered zone 121a and boundary guard zone 121b of the upper heater plate 120, as well as the central and boundary zones 129a of the lower heater plate 122, at the warm-boundary temperature can be measured. The power (e.g. measured in Watts, which equate to Joules/sec) consumed by the first heating element 128a to maintain the central metered zone 121a constant at the warm-boundary temperature provides an accurate estimate of the heat transferred from that zone 121a through the insulation 110 toward the cold-boundary temperature. Dividing the power consumption rate by the area of the central metered zone 121a gives the heat flux, which is the heat transfer rate per unit area, e.g. watts/m$^2$. Because this value is independent of the area measured, it should provide an accurate measure of the heat flux through the sample of insulation 110, even though it is measured across less than the entire lateral area of the insulation 110.

The present apparatus can be used to measure heat flux through various types of insulating material based on different cold- and warm-temperature boundary conditions. If the support members 140 are adjustable as described above, then different samples of insulation 110 having different total thicknesses also can be measured. For example, it may be desirable to determine the heat flux for different thicknesses of a particular insulating material at the same boundary conditions. Using the disclosed apparatus, different thicknesses can be accommodated through adjustment of the height of the support members 140, and consequently of the distance between the sample contact surface 123 of heater plate 120 and the outer bottom wall surface 131 of the storage vessel 130, which is preferably suspended from above. In a further alternative, it may be desirable to measure heat flux properties for a sample of insulating material at different degrees of compression. For example, one type of insulation whose heat flux performance can be measured includes layers of mylar film having Dacron netting spacers provided between adjacent mylar layers, e.g. an MLI system. The mylar film layers can be aluminized, double-aluminized, goldized, double-goldized, or alternatively provided with some other metallized coating. Alternatively, the film can be other than mylar. The netting that serves as spacers between adjacent layers can have different thread diameters, different weaves or weave or knotting patterns, or they can be made from alternative materials besides Dacron. It will be understood that such a layered insulation structure can be used totally uncompressed, in its natural expansive state (with only the weight of the layers serving to compress them). Alternatively, these layers may be compressed together to provide a more densely-packed layered structure of alternating [ . . . film-spacer-film-spacer . . . ] layers. The disclosed apparatus facilitates measurement of the heat flux characteristics of the same sample of layered insulation (or non-layered but compressible insulation) at different degrees of compression.

Figure 5A:
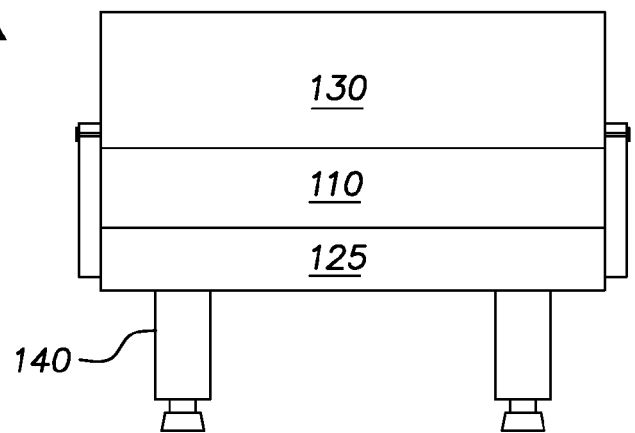
FIGS. 5a-c schematically illustrate the insulation measurement assembly of FIG. 2, at successively greater stages of compression of the sample of insulation 110 being measured, via incremental extension of the assembly support members 140.
Figure 5B:
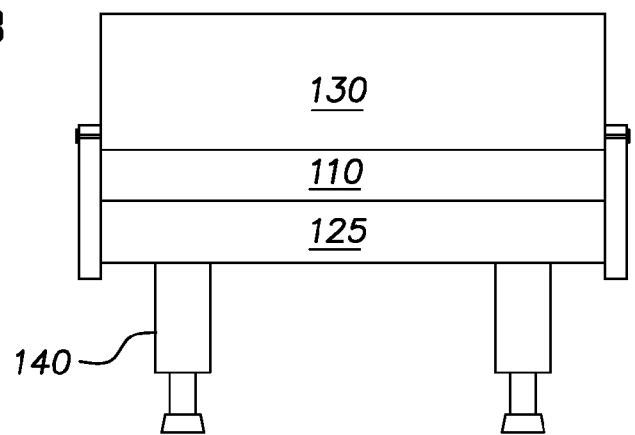
Figure 5C:
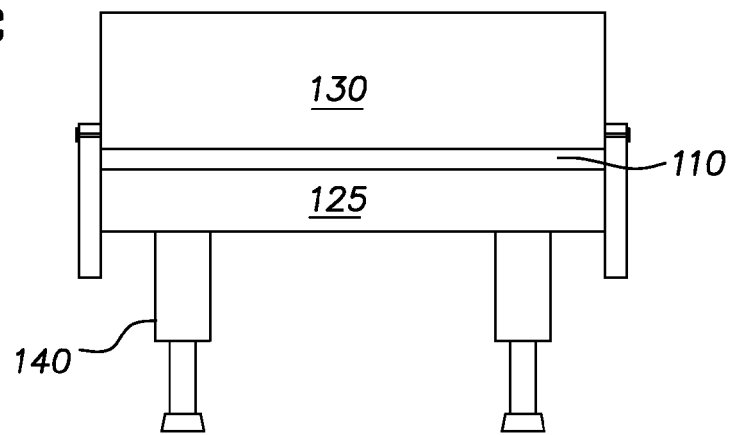

FIGS. 5a-5c illustrate this mode of operation. In FIG. 5a, the sample of insulation 110 is shown at a first state of compression, which is considered to be uncompressed. The apparatus can be operated and heat flux data obtained for the layered insulation 110 at the state of compression illustrated in FIG. 5a. Then, without disassembling the apparatus or replacing the sample 110, the support members 140 can be actuated to raise the heater arrangement 125 (sample contact surface 123) toward the vessel 130, thereby further compressing the sample of insulation 110 from the first state of compression shown in FIG. 5a, to a second, more compressed state of compression shown in FIG. 5b. At this new, more compressed state of compression, once again heat flux through the insulation can be measured. A third, even more compressed state of compression is shown in FIG. 5c, wherein additional heat flux data can be obtained for this higher state of compression. Operating in this manner, heat flux performance for a given sample or system of insulating material can be measured across a continuum of different insulation densities (e.g. layer densities when layered insulation is used), to determine an optimum density for performance in a specific application.

The apparatus disclosed herein is well suited to measuring heat flux through layered insulation such as conventional metallized or double-metallized (e.g. with aluminum, gold, etc.) mylar insulation with netting spacers of different configurations. This sort of insulation is commonly used to insulate cryogenic storage tanks against heat leak from the ambient environment, which can accelerate boil-off and consequent wasteful loss of cryogenic material. Such insulation is commonly used in space-based applications, where large amounts of cryogenic material often must be stored for long periods of time. The heat-transfer rate through such insulation materials is very low, meaning that even very low rates of heat exchange between the sample of insulation 110 and the ambient environment can introduce relatively significant errors in the heat flux calculation between the warm- and cold-temperature boundaries in the z-direction (from heater plate 120 to outer bottom wall surface 131). One way to counteract or inhibit ambient heat transfer to/from the sample of insulation 110 is to enclose the entire insulation measurement assembly 100 within a vacuum chamber 200 as shown. The absence of air or other gas in the space surrounding the assembly 100 (and the insulation 110) substantially eliminates two primary modes of heat exchange with the environment, conduction and convection. However, radiation heat transfer, for example between the walls of the vacuum chamber 200 and the edge or perimeter of the sample of insulation 110, is still possible.

To counteract edge-effect radiation heat transfer to or from the sample of insulation, a thermal guard skirt 150 is preferably employed. In a preferred embodiment, the skirt 150 is secured at an upper edge thereof to the sidewall of the cryogenic storage vessel 130, about the circumference thereof via bolts 154 or other conventional or suitable fasteners. In this embodiment, it is desirable that the skirt 150 be made from the same material as the cryogenic storage vessel 130, such as stainless steel. This will prevent unmatched thermal expansion between the skirt 150 and the vessel 130 from compromising the attachment between them. It also will prevent the introduction of additional variables or error based on heat leak around a misshapen skirt 150 due to unmatched expansion with the vessel to which it is attached. Alternatively, the skirt 150 can be made from a different material, for example conventional G-10 insulation as known in the art. In this embodiment, it will be desirable to employ a fastening system that minimizes thermal contact resistance between the vessel 130 wall and the skirt 150, or improves intimate physical contact between them, so as to minimize unmatched thermal expansion effects. The skirt 150 extends downward from the storage vessel 130 to a sufficient extent so that it extends at least beyond the lower surface 114 of the sample of insulation 110 once that sample 110 is sandwiched between the vessel 130 and the heater plate 120. In a preferred embodiment, a vertical temperature gradient is developed in the skirt 150, in the region thereof adjacent the perimeter of the insulation 110, which approximates the known or anticipated vertical temperature gradient induced in the insulation 110 between the hot- and cold-boundary temperatures at steady state. One way to provide a vertical temperature gradient is to wrap a heating element such as heater tape circumferentially about the skirt 150 at one or more vertical locations, and then to operate that/those heater tape(s) to develop the desired vertical temperature gradient. If a skirt 150 is used, care should be taken when lowering the storage vessel 130 (with skirt 150 secured thereto) to ensure the sample 110 is properly received within the skirt 150, without disturbing the co-registry of the sample 110 with either surface 123 or 131.

In a further embodiment, a circumferential temperature guard 170 is disposed around the insulation measurement assembly 100, spaced therefrom and also from the sidewall of the vacuum chamber 200. The temperature guard 170 also preferably includes a base portion that extends parallel to the base 230 of the vacuum chamber 200, underneath the heater arrangement 125. The guard 170 is preferably made from the same material as the heater plates 120 and 122 (stainless steel), and is maintained at the same temperature as those plates (i.e. at the warm-boundary temperature). This ensures that the environmental temperature around the assembly 100 (and particularly the sample of insulation 110) is consistent between tests or on different days, regardless of the actual temperature of the vacuum chamber 200, which can be influenced by external factors such as the weather. In other words, the guard 170 ensures the MLI test sample sees the same external temperature, regardless of the vacuum chamber wall temperature. This way, to the extent there is some small error introduced due to heat transfer from the environment, that error will be consistent among tests or on different days.

Figure 6:
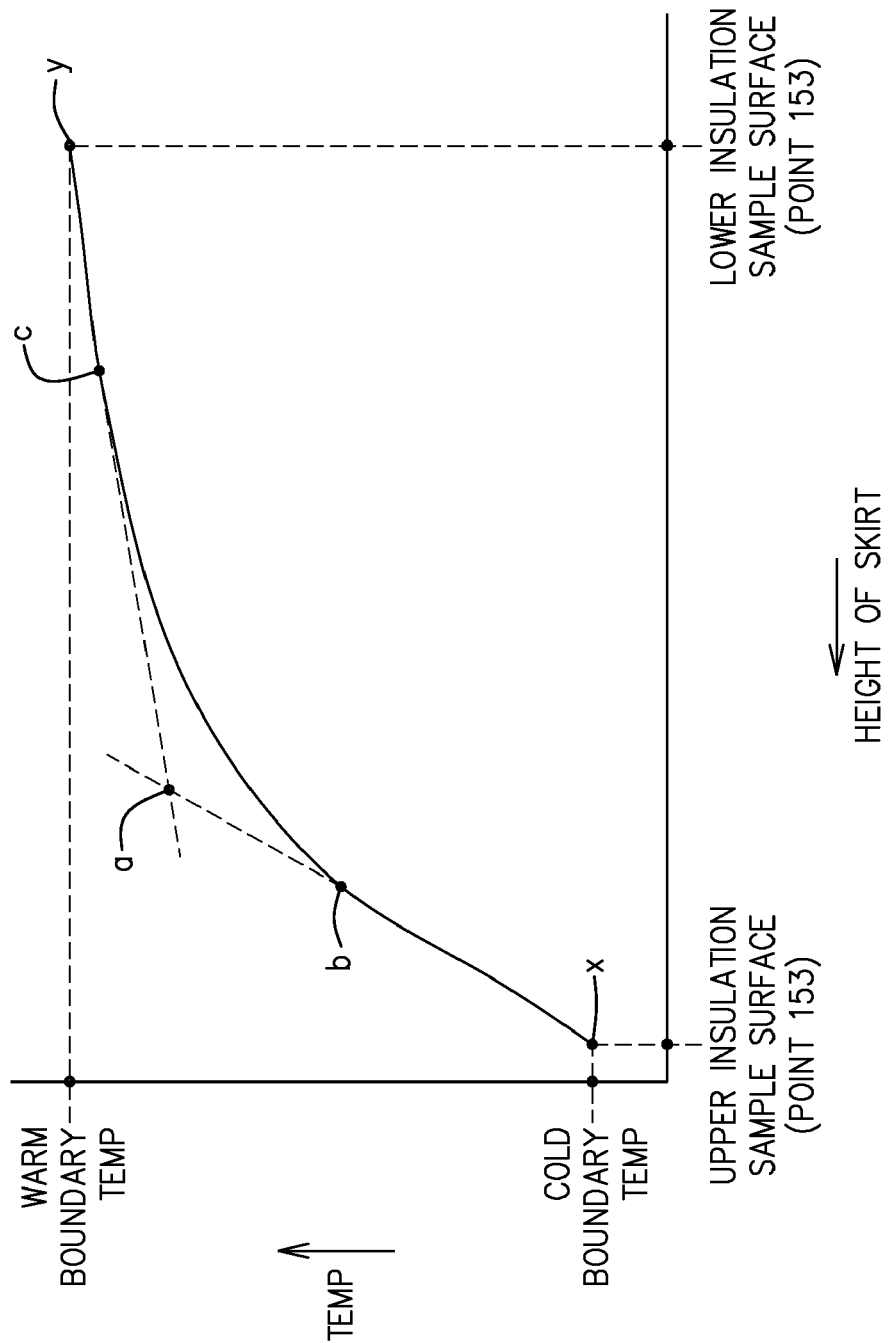
FIG. 6 illustrates a temperature profile for the thermal skirt 150, which approximates that measured from the base of the cryogenic tank 130 above the insulation sample 110, to the heater arrangement 125 under the insulation sample 110.

In a preferred mode of operation, wherein radiation heat flux is to be measured through a sample of layered metallized mylar insulation with spacers, the vertical temperature gradient through the insulation sample 110 will be nonlinear as shown in FIG. 6. Briefly, as known in the art, the driving force for radiation heat transfer is the temperature of the radiating body to the fourth power ($T^4$), and not simply the linear difference between two temperatures ($\Delta T$) as in conductive heat transfer. The $T^4$ term contributes to the curvature in the temperature profile seen in FIG. 6, which would be expected when radiation is the dominant heat transfer mode. In this case, the vertical location(s) of the heater tape(s) wrapped around the circumference of the skirt 150 can be selected based on the known or anticipated temperature gradient in the sample of insulation 110, and operated to induce a similar gradient profile vertically in the skirt 150.

For example, in FIG. 6, the temperature gradient profile has two substantially linear regions located proximate the cold-temperature boundary and the warm-temperature boundary, respectively. An arcuate region of the temperature profile exists between the two substantially linear regions. Based on this profile, one heater tape could be provided at the vertical location (height) of the skirt 150 corresponding to point "a," which is determined through linear extrapolation from the substantially linear portions of the gradient profile. The one heater tape then can be operated at the temperature corresponding to point "a" in FIG. 6, which would produce two linear temperature gradients similar to the broken extrapolation lines in the figure, assuming the skirt is in contact with the cold- and warm-temperature boundaries at points "x" and "y," respectively. Alternatively, if a closer approximation of the actual temperature profile in FIG. 6 is desired, then two heater tapes could be used, e.g. at the vertical locations on the skirt corresponding to points "b" and "c" in FIG. 6, and operated at the correspondingly indicated temperatures. This should produce a three-segment temperature profile in the skirt 150 that more nearly approximates the true temperature gradient shown in FIG. 6 than the two-segment profile based on only one heater tape located at point "a."

In one embodiment, the skirt 150 can be provided with a series of heater tapes 155 wrapped circumferentially about its surface at spaced intervals, as shown in FIG. 2. Because the known or anticipated temperature profile in each sample of insulation 110 to be tested may be different from sample to sample, only those heater tapes 155 desirable to approximate the desired temperature profile in a given instance need to be actuated. For example, in the case where heater tapes 155 corresponding to vertical locations "b" and "c" in FIG. 6 need to be used to approximate a desired temperature profile, only those two heater tapes 155 would be actuated, to produce the appropriate temperatures, with all the remaining tapes 155 left off. The power supplied to each heater tape 155 can be individually controlled to produce the desired heating power to maintain the desired temperature at the corresponding vertical position of the skirt 150.

Returning to FIG. 6, the cold- and warm-boundary temperatures are test variables selected by the experimenter; accordingly, they are known values. Likewise, the height of the skirt 150 between the cold- and warm-boundary temperatures also is known, based on the height of the insulation sample 110 to be tested, or the distance between the surfaces 123 and 131 if the insulation sample 110 is to be compressed. Accordingly, the upper and lower boundary conditions for both the ordinate and abscissa axes in FIG. 6 will be known, fixed values for any test. The shape of the curve in between can be determined iteratively by actually running an experiment and measuring the gradient in the sample 110, or through calculation if sufficient parameters regarding expected insulation performance are known from literature or past experiments. It is contemplated that in some instances, an iterative procedure that combines both techniques might be employed, for example where literature data provide an initial approximation for the expected temperature profile, which can then be verified or modified based on actual experimental data.

When layered insulation materials such as MLI with netting spacers are the sample 110 being tested, radiation heat transfer would be expected to dominate when the layers are uncompressed, thus producing a curved temperature gradient. However, operation of the apparatus to compress a layered sample 110 would raise the layer density and increase layer-to-layer contact, which may be expected to linearize the temperature profile because conduction heat transfer may become more prevalent with increased contact between layers. At some point, when the layers are highly compressed so that adjacent layers are essentially in intimate contact with one another, a truly linear profile may be achieved, even for layered-insulation samples 110. These effects should be taken into account, and may need to be determined experimentally prior to generating a corresponding temperature profile in the skirt 150 to minimize edge-effect radiative heat transfer to or from the perimeter of the sample 110.

As will be most clearly appreciated from FIGS. 5a-5c, the portion of the skirt 150 adjacent the edge or perimeter of the insulation sample 110 may change from sample to sample, and even for the same sample at different degrees of compression. By providing a series of heater tapes 155 extending circumferentially of the skirt 150 at spaced height intervals (see FIG. 2), only the appropriate heater tapes 155, at appropriate height locations for a given sample 110 (or at different degrees of compression for the same sample 110) need be actuated to shield against edge-effect radiation to/from the sample 110. Other heater tapes can remain off. Hence, the series of heater tapes 155, spaced across a substantial portion of the height of the skirt 150, can eliminate the need to reposition or reapply heater tapes at appropriate heights based on a particular sample 110 to be tested. The present configuration enables the skirt 150 to be reused for all samples whose height is less than that of the skirt 150, without having to be reconfigured based on each sample.

From the foregoing, it will be evident that the cryogenic liquid provided in the storage vessel 130 is used solely to provide the desired cold-boundary temperature at the outer bottom wall surface 131 of the vessel 130. Consequently, there is no need to measure or quantify the amount of cryogenic material that is evaporated through boil-off and vented. The amount of vented cryogen is irrelevant to calculating the measured heat flux through the sample of insulation 110. This is a significant advance over the state of the art with respect to quantifying low heat flux through layered insulation systems. Conventional methods rely on measuring the amount of lost cryogen, and then back-calculating the heat flux based on the area of the vessel in contact with the insulation and the latent heat of evaporation for the cryogenic material. Such methods produce significant errors, both experimental and analytical because 1) the rates of cryogen boil-off are very low, and thus difficult to accurately quantify with existing equipment, and 2) it is very difficult to accurately account for or prevent other modes of heat transfer to the cryogenic vessel which also can contribute to boil-off of cryogenic material in an unpredictable way.

Conversely, the present method and apparatus measure the power necessary to maintain the warm-boundary temperature directly, across a known and fixed area. That fixed area (the central metered zone 121a) is operated adiabatically except for flux in the direction of the insulation 110, so the power necessary to maintain its temperature provides an accurate measure of that flux. No measurement of boil-off is required, and no special precautions need to be taken to prevent or measure other sources of heat leak into the cryogenic storage vessel. It should be noted, however, that one may optionally include apparatus to measure boil-off of the cryogenic material, for example if it is desirable to know how much cryogen is released to the atmosphere from an environmental standpoint. But it should be clear that no such measurement is required for proper operation of the apparatus.

Although the hereinabove described embodiments of the invention constitute preferred embodiments, it should be understood that modifications can be made thereto without departing from the spirit and the scope of the invention as set forth in the appended claims.

What is claimed is:

1. An apparatus to measure insulation thermal performance, comprising a warm-temperature boundary having a continuous thermally-conductive sample contact surface and a cold-temperature boundary, said continuous sample contact surface having a central metered zone and a boundary guard zone surrounding said central metered zone, both said central metered zone and said boundary guard zone being heated zones and said central metered zone being heated independently of said boundary guard zone, wherein said apparatus is adapted to accommodate a sample of insulation between said sample contact surface and said cold-temperature boundary for measuring heat flux through the sample.

2. The apparatus of claim 1, further comprising a vacuum chamber, said warm-temperature boundary and said cold-temperature boundary being disposed within said vacuum chamber.

3. The apparatus of claim 1, further comprising a skirt of insulating material adapted to surround said sample of insulation, adjacent a perimeter thereof, when said sample is disposed between said sample contact surface and said cold-temperature boundary.

4. The apparatus of claim 1, comprising:
a heater arrangement comprising a first heater plate and a second heater plate fixed in spaced parallel relationship, said sample contact surface being a surface of said first heater plate facing away from said second heater plate;
a first heating element adapted to supply heat to the central metered zone and a second heating element adapted to supply heat to the boundary guard zone; and
a third heating element adapted to supply heat to said second heater plate;
said first, second and third heating elements being independently operable.

5. The apparatus of claim 4, said first heating element contacting said first heater plate and being coextensive and in register with the central metered zone of said sample contact surface, and said second heating element contacting said first heater plate and being coextensive and in register with the boundary guard zone of said sample contact surface.

6. The apparatus of claim 4, further comprising insulation material disposed in the space between said first and second heater plates.

7. The apparatus of claim 4, said second and third heating elements being operable to maintain said boundary guard zone and said third heater plate, respectively, at the same temperature as said central metered zone, whereby said central metered zone is operable adiabatically except in a direction toward said cold-temperature boundary, wherein power supplied to said first heating element to maintain said central metered zone at constant temperature is directly equatable to heat flux from said central metered zone.

8. The apparatus of claim 4, said first and second heater plates being coextensive and in register with one another.

9. The apparatus of claim 4, said second heater plate being a continuous plate and having a second central zone and a second boundary guard zone coextensive and provided in register with said central metered zone and said boundary guard zone, respectively, of the first heater plate, said third heating element being adapted to supply heat to said second central zone of said second heater plate, the apparatus further comprising a fourth heating element adapted to supply heat to said second boundary guard zone of said second heater plate, wherein said fourth heating element is independently operable from said first, second and third heating elements.

10. The apparatus of claim 4, said first heating element comprising a printed circuit having resistive copper traces in the form of a series of evenly-spaced concentric rings with electrical connections provided between adjacent rings.

11. The apparatus of claim 4, said second heating element comprising an array of printed circuit segments aligned around said first heating element, each said segment comprising resistive copper traces in the form of a series of evenly-space concentric arcs with electrical connections provided between adjacent arcs such that a single resistive circuit is formed in each segment.

12. The apparatus of claim 11, wherein all said printed circuit segments are electrically connected in series to provide said second heating element.

13. The apparatus of claim 4, said sample contact surface being a substantially horizontal surface, the apparatus further comprising a cryogenic storage vessel suspended above said sample contact surface, and having an outer bottom wall surface facing said sample contact surface, said outer bottom wall surface of said cryogenic storage vessel defining said cold-temperature boundary.

14. The apparatus of claim 13, said sample contact surface and said outer bottom wall surface both being circular, and disposed in register with and parallel to one another.

15. The apparatus of claim 13, further comprising a vacuum chamber, said heater arrangement and said cryogenic storage vessel being disposed within said vacuum chamber.

16. The apparatus of claim 15, said cryogenic storage vessel being suspended from a removable lid of said vacuum chamber.

17. The apparatus of claim 13, further comprising a skirt of insulating material adapted to surround said sample of insulation, adjacent a perimeter thereof, when said sample is disposed between said sample contact surface and said outer bottom wall surface.

18. The apparatus of claim 17, said skirt of insulating material further comprising a series of heating elements operable and adapted to develop a predetermined temperature profile in said skirt that approximates an anticipated or known temperature profile in said sample of insulation during operation of said apparatus.

19. The apparatus of claim 13, the height of said heater arrangement being supported by an adjustable support system capable to raise and lower said heater arrangement to thereby adjust the distance between said sample contact surface and said outer bottom wall surface of said cryogenic storage vessel.

20. The apparatus of claim 4, said adjustable support system comprising a vertical actuator device coupled to and supporting said heater arrangement via a gimbal joint.

21. The apparatus of claim 20, said adjustable support system comprising a plurality of said vertical actuator devices, each coupled to and supporting said heater arrangement via a respective gimbal joint, wherein the vertical actuator devices are thus independently operable to adjust the height and planar orientation of the heater arrangement.

22. The apparatus of claim 20, further comprising a vacuum chamber having a base, said heater arrangement being disposed within said vacuum chamber, said vertical actuator device being aligned with and extending through an opening through said base, wherein said opening is sealed so as to provide a vacuum-tight seal during operation of said apparatus.

23. The apparatus of claim 22, said opening being sealed via an extensible bellows disposed around said vertical actuator device.

24. An apparatus to measure insulation thermal performance, comprising a warm-temperature boundary having a continuous sample contact surface and a cryogenic storage vessel having an outer surface adapted to provide a cold-temperature boundary, said continuous sample contact surface having a central metered zone and a boundary guard zone surrounding said central metered zone, both said central metered zone and said boundary guard zone being heated zones and said central metered zone being heated independently of said boundary guard zone, wherein said apparatus is adapted to accommodate a sample of insulation between said sample contact surface and said cold-temperature boundary for measuring heat flux through the sample.

25. The apparatus of claim 24, wherein the distance between said sample contact surface and said outer surface of said storage vessel is adjustable.

26. A method for measuring thermal performance of a sample of insulation, comprising:
a) providing an apparatus to measure insulation thermal performance, comprising a warm-temperature boundary having a continuous sample contact surface and a cold-temperature boundary, said continuous sample contact surface having a central metered zone and a boundary guard zone surrounding said central metered zone, both said central metered zone and said boundary guard zone being heated zones and said central metered zone being heated independently of said boundary guard zone, wherein said apparatus is adapted to accommodate a sample of insulation between said sample contact surface and said cold-temperature boundary for measuring heat flux through the sample;
b) providing a cryogenic storage vessel having an outer surface;
c) disposing a sample of insulation between said sample contact surface and said storage vessel outer surface;
d) separately maintaining said central metered zone and said boundary guard zone at a constant warm-boundary temperature;
e) measuring the power required to separately maintain said central metered zone at said constant warm-boundary temperature; and
f) equating said power to heat flux through said sample of insulation.

27. The method of claim 26, further comprising providing a skirt of insulating material having a series of heating elements surrounding the perimeter of said sample of insulation, and operating said series of heating elements to develop a temperature profile in said skirt that approximates an anticipated or known temperature profile in said sample of insulation.

28. The method of claim 26, said apparatus comprising
a heater arrangement comprising a first heater plate and a second heater plate fixed in spaced parallel relationship with said first heater plate, said sample contact surface being a surface of said first heater plate facing away from said second heater plate;
the method further comprising maintaining said boundary guard zone and said third heater plate at the same temperature as said central metered zone, wherein said central metered zone is operated adiabatically except in a direction toward said cold-temperature boundary.

29. The method of claim 28, said heater arrangement further comprising first and second heating elements in contact with the first heater plate, said first heating element being adapted to supply heat to the central metered zone and said second heating element being adapted to supply heat to the boundary guard zone; and
a third heating element in contact with the second heater plate adapted to supply heat thereto;
said first, second and third heating elements being independently operable to independently heat said central metered zone, said boundary guard zone and said second heater plate, respectively.

\* \* \* \* \*

UNITED STATES PATENT AND TRADEMARK OFFICE
CERTIFICATE OF CORRECTION

PATENT NO. : 7,540,656 B1 Page 1 of 1
APPLICATION NO. : 11/627783
DATED : June 2, 2009
INVENTOR(S) : Stochl et al.

It is certified that error appears in the above-identified patent and that said Letters Patent is hereby corrected as shown below:

In Col. 16 Claim 20 at line 59, replace "claim 4" with "claim 19."

Signed and Sealed this

Eighteenth Day of August, 2009

David J. Kappos
*Director of the United States Patent and Trademark Office*